United States Patent
Blanc et al.

(10) Patent No.: US 9,174,245 B2
(45) Date of Patent: Nov. 3, 2015

(54) SYSTEM FOR THE AUTOMATIC SELECTIVE SEPARATION OF ROTTEN CITRUS FRUITS

(75) Inventors: Philippe Gabriel Rene Blanc, Alzira (ES); Jose Blasco Ivars, Alzira (ES); Enrique Molto Garcia, Alzira (ES); Juan Gomez Sanchis, Alzira (ES); Sergio Cubero Garcia, Alzira (ES)

(73) Assignee: RODA IBERICA, S.L.U., Alzira (Valencia) (ES)

( * ) Notice: Subject to any disclaimer, the term of this patent is extended or adjusted under 35 U.S.C. 154(b) by 981 days.

(21) Appl. No.: 12/312,160

(22) PCT Filed: Feb. 26, 2008

(86) PCT No.: PCT/ES2008/070030
§ 371 (c)(1),
(2), (4) Date: Nov. 19, 2009

(87) PCT Pub. No.: WO2008/104627
PCT Pub. Date: Sep. 4, 2008

(65) Prior Publication Data
US 2010/0121484 A1    May 13, 2010

(30) Foreign Application Priority Data

Feb. 27, 2007   (ES) .................................. 200700514
Feb. 26, 2008   (ES) .................................. 200800528

(51) Int. Cl.
*B07C 5/342*    (2006.01)
*B07C 5/36*     (2006.01)
*G01N 21/85*    (2006.01)
*G01N 21/84*    (2006.01)

(52) U.S. Cl.
CPC ............... *B07C 5/3422* (2013.01); *B07C 5/363* (2013.01); *G01N 21/85* (2013.01); *G01N 2021/845* (2013.01); *G01N 2021/8466* (2013.01)

(58) Field of Classification Search
CPC .............................. B07C 5/342; B07C 5/3422
USPC ........... 700/228, 229, 230, 231, 244; 209/578
See application file for complete search history.

(56) References Cited

U.S. PATENT DOCUMENTS 4,735,323 A * 4/1988 Okada et al. .................. 209/582
5,164,795 A * 11/1992 Conway ........................ 356/407
5,388,707 A * 2/1995 Stivison et al. ............... 209/602

(Continued)

FOREIGN PATENT DOCUMENTS

ES         2 081 231       2/1996
WO      WO 98/17406      4/1998
WO     WO 2006/058406    6/2006

*Primary Examiner* — Patrick Mackey
(74) *Attorney, Agent, or Firm* — Michael J. Striker

(57) ABSTRACT

The invention relates to system conceived and designed to identify pieces of fruit, especially citrus fruits, affected by any amount of rot and to determine the automatic expulsion of these pieces from the conveyor moving them through the installation. The system comprises illuminating the fruits with UV-A band light in a computer vision unit, and capturing images of the illuminated fruits by means of a camera to send them to a general control member in order to detect fluorescences associated to the rot effect. The identified fruit is automatically expelled from the conveyor in an expulsion unit, the position of the defective fruit being determined with the aid of an encoder associated to the conveyor. The general control member is a PC type computer, equipped with specific application software.

7 Claims, 3 Drawing Sheets

(56) References Cited

U.S. PATENT DOCUMENTS 5,440,127 A * 8/1995 Squyres .................... 250/341.8
6,374,983 B1 * 4/2002 Morigi ..................... 198/370.07
6,410,872 B2 * 6/2002 Campbell et al. ............. 209/577
6,536,598 B2 * 3/2003 Furnas ......................... 209/523

* cited by examiner

SYSTEM FOR THE AUTOMATIC SELECTIVE SEPARATION OF ROTTEN CITRUS FRUITS

OBJECT OF THE INVENTION

The present invention relates to a system for the automatic selective separation of rotten citrus fruits, providing essential features of novelty and considerable advantages with respect to the means known and used for the same purposes in the current state of the art.

More particularly, the invention proposes developing a highly efficient system for the identification of pieces of citrus fruits affected by rot problems, and their automatic removal from a product classification line prior to packaging the citrus fruits, for which purpose the system incorporates a UV light emission unit, closed to the outside, forming the vision unit in which UV light is projected on the pieces of citrus fruits traversing it on a conveyor, and the condition of the citrus fruits is determined in accordance with the nature of the fluorescence observed thereon and captured by camera after being filtered. An encoder controls the position of the unwanted pieces for their automatic separation when they reach the expulsion unit located after the mentioned vision unit. In an alternative embodiment, the damaged fruits are identified by a combined action of a fluorescence effect and of an image loss effect, in relation to the images captured by means of two cameras incorporated in the vision unit in opposite aligned positions in relation to a line transverse to the movement of the fruits.

The field of application of the invention is comprised within the industrial sector dedicate to the construction and installation of automatic classification and recognition devices, particularly those intended for the fruit and vegetable sector.

BACKGROUND AND SUMMARY OF THE INVENTION

Persons skilled in the art know that the cultivation of citrus fruits is the main national fruit sector. Half the citrus fruits produced in Spain are intended for export, therefore Spanish citrus fruits occupy a very important place in the context of producer countries. However, the low production costs of non-European countries of the Mediterranean area allow their citriculture to compete advantageously on the market against Spanish productions. If this is added to the progressive opening of the European Union markets to these countries, the only alternatives that seem to be possible for maintaining the market share consist of offering a product with a better quality than the competing countries, together with a reduction in the production costs.

The quality of the fruit is determined by aspects such as the presentation, the appearance, the uniformity, the ripeness and the freshness, all of them being essential components of the purchase decision. The quality of the fruits can be affected by various reasons, giving rise to morphological and physiological defects devaluating the product. The most worrying causes include those generating defects in the fruit during or after the preparation for the market, and which show in the places of sale. The mechanical damage or lesions taking place while handling the product are the entryway for multiple pathogens causing rot, such as fungi of the *Botrytis, Rhizopus, Alternaria, Geotrichum* genera, but especially the *Penicillium digitatum* (green mold) and *Penicillium italicum* (blue mold) fungi, causing most of the post-harvest infections.

Losses due to rot are of the order of 3-5% of all the fruits handled in centers, reaching the order of 7-12% in abnormal weather years. To reduce these losses, several sorting operations are carried out in the fruit processing plant, considering criteria such as defects in the skin, presence of insects, damage due to hail, deformed fruits, etc. However, this operation is not always effective due to the possibility that, at the time of the sorting, the damage caused by rot is still not externally visible. In these conditions, the fungus will develop during storage and transport, spreading the infection throughout the entire batch and causing large economic losses. A quick detection of the infection will be especially important to maintain the quality of the product and prevent economic losses to thus be able to compete in better conditions on the market.

The use of ultraviolet light to detect the infection in the fruit before it develops externally is currently known in the state of the art. The known method is essentially based on the fact that, when the infection caused by the fungus progresses, the chemical composition of the fruit tissues is altered, the essential oils contained in the glands of the skin being spilled; the illumination of these tissues with UV light shows their fluorescence, making damage which is still latent visible.

UV rays form the band of the electromagnetic spectrum comprised between 100-400 nm, adjoining X-rays and the visible band. The light is generally divided into three bands with the following wavelengths: UV-C, 100-280 nm; UV-B, 280-315 nm; UV-A, 315-400 nm.

The sorting operation making use of UV light is carried out manually in special inspection chambers located in the processing line and usually known as "discotheques". These chambers consist of dark cabinets, with small dimensions, illuminated only with black light tubes; these tubes emit a wavelength corresponding with the UV-A band. The fruit developing fluorescence upon passing through the cabinet indicates that the infection is latent and will be immediately eliminated from the line. The fruits pass over rollers rotating and making the fruits rotate such that substantially the entire surface of the fruit can be seen.

However, the use of UV light in this mode of inspection has several drawbacks. In fact, UV radiations are, among non-ionizing radiations, those with the greatest energy content. This relatively high energy content makes them capable of chemically reacting with matter, causing the so-called photochemical reactions. The biological effects of UV rays mainly affect the skin, causing erythemas, loss of elasticity and delayed melanogenesis. This type of radiation can also cause ophthalmic diseases such as keratitis, conjunctivitis and cataracts. For these reasons, UV lamps are considered a Group I risk by the *Illuminating Engineering Society* (ANSI/IESNA RP-27.3-96).

Practical recommendations have been established for the safe photo-biological use of UV light lamps. These recommendations are based on tolerable radiation limits. Thus, for lamps emitting radiation with wavelengths comprised between 320 and 400 nm, the energy flow must not exceed 1 mW/cm$^2$ and the exposure time must be limited, to a greater extent the lower the distance to the emitting source. According to these recommendations, the operators working in these inspection cabinets work in shifts in order to not remain in the cabinets for a time greater than one hour. Another recommendation consists of using protective gloves and goggles absorbing the UV radiation received, reducing the exposure of the operator to non-hazardous levels (RD-773/1997 and RD-1002/2002). Specific and periodic medical examinations and radiation measurements will be carried out to control these aspects.

The manual selection work in these conditions is tedious and repetitive for the operators. Additionally, this labor represents a considerable cost for the company.

Analysis techniques have therefore progressed during the last few years for the purpose of achieving fruit classification and rejection systems which allow reducing the high personnel costs directly related to this process. In this sense, the automation of these tasks will allow improving the quality of the work of these operators, since it is carried out automatically, the job of the operator being limited to supervising the correct operation of the system from the outside through control monitors.

There is currently no knowledge of the existence on the market of an automatic system which allows detecting rot of fruits making use of the fluorescence of the essential oils upon applying UV light, despite the intense research being conducted in relation to this type of system.

The present invention belongs to the sector of the systems responsible for the detection of pieces of fruit, especially citrus fruits, having any amount of rot, and has been developed for the purpose of providing effective solutions to the problems existing in the installations of the current state of the art. This objective has been fully reached by means of the system the embodiments of which will be the object of the description below, and the main features of which are included in the characterizing portion of the attached claim 1. The dependent claims define the details and particulars of the system of the invention.

The system of the invention is essentially intended for the physical separation of the fruits having any type of rot passing through a treatment and calibration line, by means of the automatic expulsion of the affected fruits, and it therefore automatically carries out the same job which was being performed manually up until now.

The operation principle of the system is based on using black light, more specifically light belonging to the UV-A band, to detect the rot which may be developing in citrus fruits, in the same way as it is used in manual sorting. To that end, the system uses the observed feature that the essential oils coming out during the development of the rot react when UV light impinges on them, emitting fluorescence. This fluorescence is a radiation with rather low intensity, and with a very important component of wavelengths centered in the green-yellow band. This fluorescence is that identified in the images captured by a camera to determine if the fruit is affected by any type of rot.

To achieve this objective, a system has been designed which in its preferred embodiment comprises a first unit acting as a computer vision member, in which the fruit passing on a conveyor means is illuminated with ultraviolet light, such that in the event that any rot is detected on one or more specific pieces, the fluorescence emitted by the latter will be captured by the computer vision system. This situation is detected by the identification and control member, preferably a computer, from where a command is sent to an expulsion assembly incorporated in a corresponding unit located after the computer vision unit, such that the piece (or pieces) of citrus fruit identified as rotten are expelled from the conveyor means when they reach the corresponding position. The exact position of the piece of fruit which must be expelled is determined with the aid of a conventional encoder.

In this simple but highly efficient manner, the system identifies the rotten piece of fruit and automatically expels it from the conveyor means without needing human intervention.

Additionally, in an alternative embodiment of the invention which has been developed to perform a more precise identification of the damaged fruits, the invention has provided several modifications intended to improve the functionality of the described system by means of providing other alternative capacities complementary to those implemented by the first embodiment and aimed at a more perfect view of the fruits when they pass through the installation with better selection assurances.

Essentially, these improvements proposed by the second embodiment of the present invention basically consist of a change in the number and in the position of the computer vision members, such that instead of a single vision member two different members are used, located in aligned opposite positions according to a line transverse to the passage of the fruits, separated by a certain distance, such that the suitably illuminated fruits are viewed from different positions, thus assuring that a much broader surface of each fruit is viewed in each case, thus eliminating possible classification errors derived from possible "dead spots" which cannot be observed with the use of a single computer vision member, despite the fact that the fruits can be rotated upon advancing through the installation.

Furthermore, to implement said second embodiment, a thorough selection of the computer vision members has been carried out, based on MAF type cameras equipped with 2 monochromatic sensors, one of which is intended for the detection of fluorescences and the other of which, equipped with suitable NIR filters, allows observing slight variations in the images caused by the impingement on the damaged area of the small near IR component inherent to UV light emitted to illuminate the fruits when they pass through the detection area.

BRIEF DESCRIPTION OF THE DRAWINGS

These and other features and advantages of the invention will be shown more clearly from the following detailed description of a preferred embodiment given solely by way of an illustrative and non-limiting example, with reference to the attached drawings, in which.

DESCRIPTION OF A PREFERRED EMBODIMENT

Figure 1:
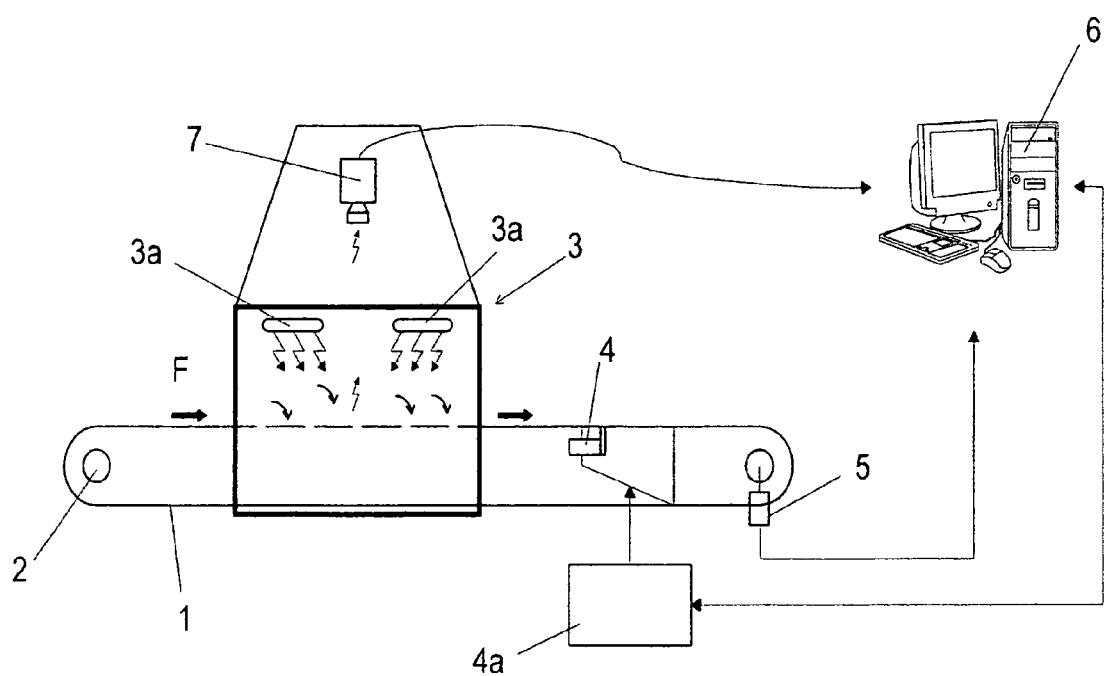
FIG. 1 shows a schematic diagram of the system assembly according to a first embodiment of the invention.

As has been mentioned above, the detailed description of the preferred embodiments of the present invention will be made below with the aid of the attached drawings, FIG. 1 of which shows a schematic depiction of a first embodiment of the system of the invention. If the graphic depiction of said FIG. 1 is observed, it can be seen that the depicted assembly comprises several differentiated sections, each of which has been include to fulfill a specific mission, and among which the following are distinguished:

a conveyor 1 extended between end rollers 2, moving by being driven in a travel direction of the fruit which, in the depicted example, corresponds with the direction of arrow F;

a first unit forming the computer vision member, generally designated with 3, provided both for illuminating the citrus fruits and to capture images in relation to the possible fluorescences shown by defective pieces of fruit;

an expulsion unit, designated with reference number 4 and located downstream from the first unit 3, in which means have been incorporated to expel the pieces of fruit identified as rotten from the conveyor 1;

an encoder device 5, intended to accurately determine the position of the rotten pieces of fruit which must be expelled from the conveyor when they pass through the expulsion unit 4, and a control unit 6, preferably consisting of a PC type computer, and provided with specific application software designed in accordance with the different functions of the system.

The conveyor device 1, depicted only in a schematic manner, can be chosen from a plurality of conveyors known in the state of the art, provided that it is capable of providing a sufficient rotation of the pieces of citrus fruits which allows determining those which, as explained above, may be possibly affected by rot problems. In a preferred form of implementation of the system of the invention corresponding to this first embodiment depicted in FIG. 1, the conveyor consists of a fruit rotating and conveying element of the type incorporating bicones and lever expellers (manufactured and marketed by the company MAF RODA). The conveyor assembly essentially consists of conveyor chains supported on guides, to which chains there are coupled biconic rubber-coated cylinders known as "bicones", capable of rotating freely. Due to the shape of the bicones and of the fruit, all the fruits can be arranged in an aligned manner, one after the other. Before reaching the chamber of the first unit 1, the mentioned bicones are rotated on their axis such that the fruits are spaced out, and each gap between bicones is occupied by only one piece of fruit.

In an embodiment variant of the conveyor, the rotating bicones affect only the part of the path corresponding to the computer vision unit, forming in itself a conveyor portion independent from the rest, the operation of all the conveyor segments being duly synchronized for the purpose of allowing a safe and precise identification of any defective piece of fruit.

The type of conveyor previously mentioned in relation to the embodiment of the invention is only illustrative since it can be substituted with other equally effective versions. Thus, a conveying system is known in which the pieces of fruit located between the bicones are expelled by means of blowing pressurized air instead of using mechanical levers as described above. In this case, the system may include an electrically operated valve controlled by means of an electronic device, such that when the rotten piece of fruit faces the position of the electrically-operated valve, the electronic device determines the opening of such valve to apply a pressurized air jet driving the expulsion of the piece of fruit from the main conveyor towards its collection by another secondary conveyor.

In another embodiment, the conveying assembly can consist of one known technically as a "hand" conveyor, in which there is a prior segment in which the fruits are rotated, then passing to the mentioned "hand" conveyor, where hand-shaped parts, positioned horizontally with an upward concavity, are responsible for taking the pieces of fruit (one piece for every hand) towards the end of the path where said hands are actuated by means of an electromagnet to rotate and invert the position (horizontal position with the concavity downwards) and drop the fruit, then returning to the upward horizontal position such that they are again operative when they reach the beginning of the path.

Also, as an alternative conveyor assembly to those mentioned above and specifically applicable to the present invention, the conveyor known as a "cup" conveyor, with a development similar to the previous one, could be chosen, in which conveyor there are "cup"-shaped supports for the fruit.

The rotation of the cups in the corresponding position is carried out by activating a lever which releases the rear part of the cup and allows it to rock backwards by the effect of the weight.

Continuing with the description of the system shown schematically in the drawing, the computer vision unit is seen, which is referenced with the number 3, by means of which unit an enclosure is provided the inner space of which is illuminated by means of one or more sets of fluorescent tubes 3a, emitting light of the UV-A band, there furthermore being installed inside the enclosure a camera 7 for capturing images of the upper part of the fruit which passes through the inside of the unit, driven by the conveyor 1. The images captured by the camera are sent to the control member 6 through an image acquisition card (not shown) for their processing with the incorporated software programs. The bicones of the conveyor are rotated when they pass through the inside of the unit 3 so that the images of the fruits can be captured from the different surface portions thereof. According to the invention, several images of each of the fruits are taken to make up the software of the complete surface of each piece of fruit.

The compartment in which the illumination sets 3a are installed is completely closed for the purpose of preventing the negative influence of environmental light in the rot detection operation. This is due to the fact that the fluorescence created by the rot effect in the skin of the citrus fruit emits in the visible band of the spectrum, from which it can be inferred that any external disturbance would involve a source of noise while measuring the fluorescence.

As stated above, the suitable UV light source for being able to excite the fluorescence of rot is that emitted in an ultraviolet broadband, specifically in a range of between 320 nm and 400 nm.

In relation to the camera 7, the use of a type of camera based on CMOS technology is preferred, although this is not essential for capturing images. The camera 7 theoretically captures images in the visible light band, to which there has been coupled an optical filter which mainly allows light comprised in the yellow band to pass through, since this is band of the radiation in which the fluorescence of the rot effect is observed.

The connection between the camera and the control member (i.e., the computer 6) is carried out through a cable and a digital card (not shown), said card being specifically designed and developed to control the capture and acquisition of the images captured by the mentioned camera 7 from the computer 6.

Continuing in the travel direction of the conveyor 1, the fruits reach the position of the expulsion unit 4. This unit 4 has the mission of physically extracting the pieces of fruit which have been detected as rotten from the conveyor. The assembly incorporates an electronic device 4a for interaction with the control computer 6, as well as an electromagnet connected to the mentioned electronic device 4a, such that when said electromagnet is activated, it makes a lever (not visible in the figure) rotate. Each piece of fruit located between adjacent bicones is supported directly on an expelling element which, upon passing above the electromagnet when the latter is activated, rises, thus expelling the mentioned piece of fruit. Therefore, to expel a piece of fruit, a sequence consisting of the following steps occurs:

identification of a rotten piece by the computer 6;

calculation by said computer 6 of the time at which this rotten piece will reach the position of the electromagnet incorporated in the expulsion unit 4;

sending of a suitable signal from the control computer 6 to the electronic device 4a for activating the electromagnet of the expulsion unit 4, an instant before the piece of fruit reaches the mentioned expulsion position.

As is usual, a second conveyor (not shown) is responsible for collecting the expelled fruits and leading them to a reception and/or storage site.

As has been mentioned above, the system includes the incorporation of an encoder device 5 associated to the conveyor 1. This allows safely and efficiently identifying the piece of fruit which has been verified as rotten when it passes through the inside of the compartment of the computer vision unit 3. The control is performed by means of the computer 6, to which said encoder 5 is connected preferably by means of a serial port. The pulses sent from the encoder to the control computer 6 have a frequency proportional to the speed of the conveyor 1, such that since the number of pulses sent in correspondence with the travel equivalent to the distance of a bicone is known, the software installed in the control member 6 allows precisely knowing the position of each piece of fruit at all times.

Finally, as has been defined above, the control unit 6 provided by the system comprises a computer connected to the different members of said system. Said computer 6 integrates the suitable software for processing the different information and sending the corresponding signals to the desired members, based on the images captured by the camera 7 and received through the corresponding image acquisition card, until the activation at the right time of the means necessary for expelling one or more rotten pieces of fruit and the repositioning of the system to its normal operative state. It will be understood that, based on the principles set forth in the description above, a person skilled in the art can adapt the system for controlling several cameras 7 by means of a single computer 6, with the corresponding adaptation of the software, such that work can be carried out with several production lines simultaneously.

Figure 2:
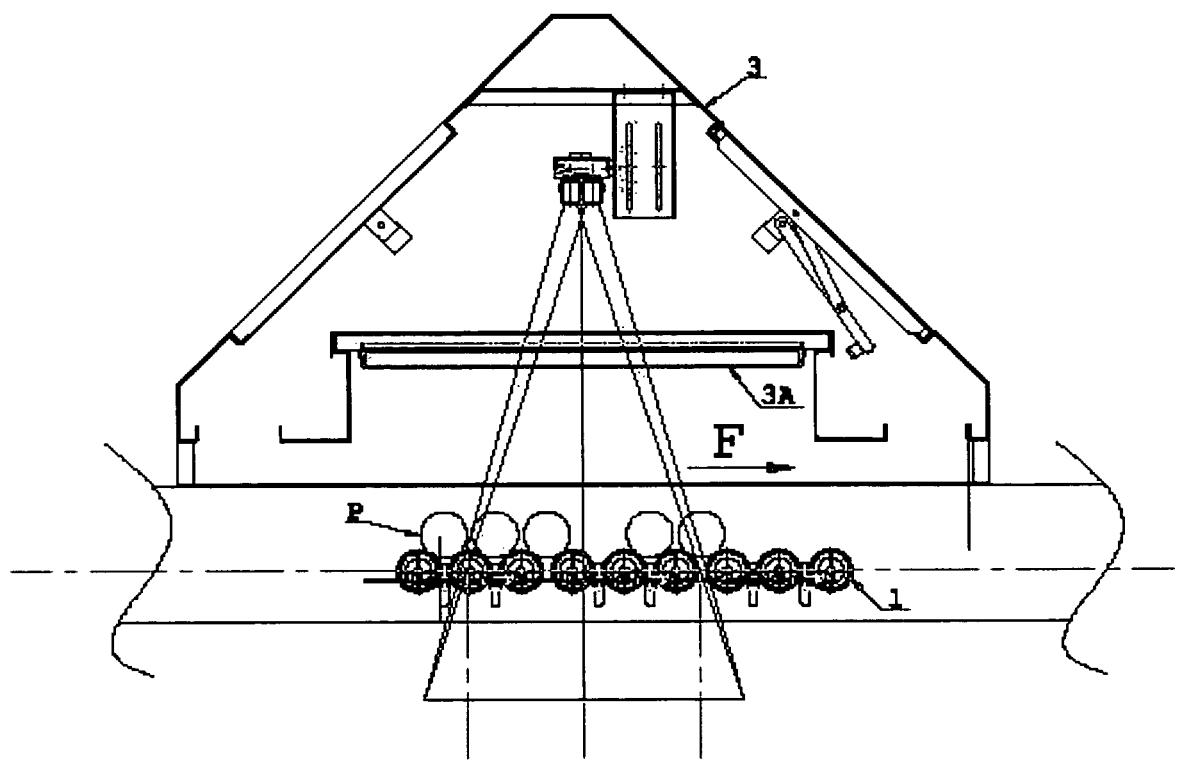
FIG. 2 shows a general schematic side elevational view of the area corresponding to the computer vision section of the system according to a second embodiment thereof.
Figure 3:
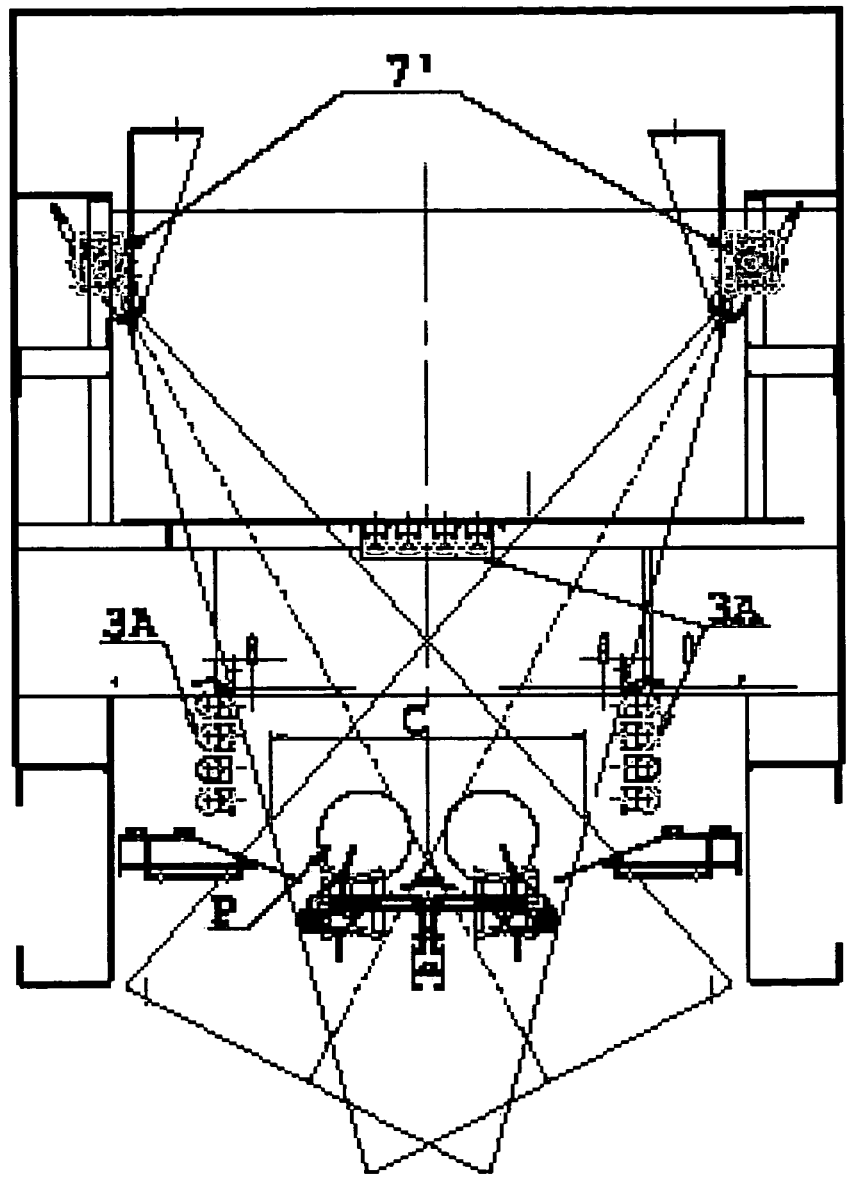
FIG. 3 is likewise a schematic illustration transverse to the computer vision unit according to the second embodiment of the system, showing the focus position of the vision members towards the passage line of the fruits which will be observed.

In relation now to FIGS. 2 and 3 of the drawings, the depiction of side elevational and cross-section views of the vision area corresponding to a second embodiment of the system proposed by the invention can be seen. To identify the different parts integrating this second embodiment of the system, reference numbers equivalent to those used in relation to the first embodiment described have been chosen in order to allow a better understand of the description and an easier identification of the different elements. Thus, first considering the depiction of FIG. 2, a general schematic side elevational view of the section of the installation corresponding to the computer vision unit can be seen, assembled above a conveyor 1 of any of the types specified in the description made above, provided for driving the products P in the longitudinal direction thereof as indicated by means of arrow F. According to this embodiment, the products are illuminated by means of UV light coming from sources 3a now arranged in positions such that they direct the highest illumination power towards the central forced passage area for the products P through the inside of the unit.

In addition, as has been stated in the description above, the viewing members are not formed by two cameras instead of a single camera as in the case of the first embodiment described. The use of two cameras located in positions previously chosen for such purpose has been determined for the purpose of assuring that the products can be observed in an amount of surface much larger than that which can be seen with a single camera, and to that end, the position chosen for both cameras is as shown in FIG. 3, in which both cameras are indicated with reference number 7', located on both sides of the drive area of the products, i.e., a camera 7' at the upper left angle and another camera 7' at the upper right angle, facing one another according to a transverse line, and such that the field of vision overlaps in a common vision area C for both cameras. With an embodiment such as the one shown, the images are taken on surface portions affecting a broad area of both sides of the fruits, whereby images of both sides synchronized with the same signal of pulses proportional to the movement speed of the fruit conveyor are provided, these images being sent to the control member (a computer, depicted in FIG. 1) for a processing and an interpretation which allows making a complete image of each product. Thus, as will be understood, the use of two cameras 7' on both sides of the passage line instead of a single camera as in the case of the first embodiment described, allows preventing "dead" spots which in another case could involved losses of information for the system, with the consequent generation of unwanted errors.

But there is another circumstance which has contributed favorably to a better identification of surface areas in which there are signs indicative of rot, and which has been able to be advantageously observed during the research conducted, with a suitable selection of MAF cameras forming each of the viewing members 7' incorporated in this embodiment of the invention. Indeed, as has been stated, usual cameras consist of two different sensors, one of which is of the monochromatic type and the other of which is of the tri-color RGB type. Up until now, only the monochromatic sensor was used, equipped with two different filters, of which a first filter allows a visible light band (between 400 nm and 700 nm) to pass through and the other filter is of the high-pass type and allows light of the spectral area located above green to pass through. The use of both sensors in an embodiment such as the one shown by the present invention was initially supposed to be able to improve the vision features of the system, since one of sensors could be used to detect the fluorescence coming from the damaged areas when they are illuminated by UV light, and the other sensor would be used to have a reference image in the blue area, such that by making a comparison between both images obtained, only the rotten areas could be highlighted. However, this form of observation had drawbacks derived from the fact that the emission of light from the UV tubes directly on the fruits gives rise to the creation of areas of brightness and shade that affect the image negatively.

Despite the foregoing, the initial supposition of improving the image with the use of both sensors associated to each of the cameras 7' has been possible by means of a suitable selection thereof. To that end, MAF cameras have been chosen in which both sensors are of the monochromatic type, and it has been observed that by assigning one of them for the observation of fluorescences in the usual manner, and by coupling suitable NIR (near infrared) filters to the other sensor for the observation of the small IR light component portion emitted by these UV tubes, a slight loss of the infrared image is seen when the rotten area is illuminated. Therefore, the simultaneous coincidence of both features (fluorescence emission and slight loss of the infrared image) unequivocally indicates that in this position there is a rotten area, thus eliminating any possibility of uncertainty or error associated to the interpretation of the data obtained.

As will be understood, the embodiment of the system which has just been described allows identifying with absolute certainty the citrus fruits having any rotten surface portion, with the consequent expulsion of these pieces from the packaging chain.

It is not considered necessary to further extend the content of this description for a person skilled in the art to understand its scope and the advantages derived from the invention, as well as to develop and put the object thereof into practice. In any case, since the system has been described in relation to a preferred embodiment thereof, the practical implementation may be susceptible to variations of detail, which may affect the types and features of the members integrating it, without departing from the scope of the invention defined by the content of the attached claims.

The invention claimed is:

1. A system for the automatic selective separation of rotten pieces of fruit, comprising:
   a conveyor for moving said pieces of fruit along a path through a processing line, with simultaneous rotation of the pieces of fruit at least in a portion of the path corresponding to an observation and viewing member;
   illumination sets configured for illuminating the pieces of fruit using light comprised in UV-A band of the spectrum to produce florescence on rotten portions of the fruit, if any;
   a computer vision unit for scanning the illuminated pieces of fruit conveyed in order to identify emitted fluorescences, wherein the computer vision unit comprises a compartment closed to the outside within which the conveyor runs, the illumination sets and two MAF cameras each with two monochromatic sensors are positioned and wherein the two MAF cameras capture the fluorescences emitted by the illuminated pieces of fruit including rotten portions;
   an automatic expulsion unit for expelling the pieces of fruit identified as rotten based on the viewed fluorescences;
   a device for controlling the position of each of the pieces of fruit identified as rotten; and
   a general system control member, connected to each and every one of the operative elements integrating the latter;
   wherein the fluorescences emitted by rotten portions of the illuminated pieces of fruit inside the computer vision unit are yellow, wherein at least one of the sensors is equipped with a filter that allows a passage of light corresponding to the yellow light spectral band and another of the sensors is equipped with a near infrared (NIR) filter to detect an infrared (IR) component associated to the emission of UV light and to allow observing a slight loss in an image generated with the sensor with the filter facing a rotten portion of one of the illuminated pieces of fruit.

2. The system according to claim 1, wherein the camera is equipped with an image acquisition card for sending images captured by said camera to the general control member.

3. The system according to claim 1, wherein the automatic expulsion unit for expelling the pieces of fruit in which rot has been detected comprises an electronic circuit controlled from the general control member, and wherein said electronic circuit activates the expelling elements associated to the conveyor.

4. The system according to claim 1, wherein the control member for controlling the position of each piece of fruit is an encoder connected to the general control member.

5. The system according to claim 1, wherein the general control member is a computer equipped with specific application software adapted to system requirements.

6. The system according to claim 1, wherein the illumination sets are located in a centered position within said computer vision unit in order to project a considerable light power directed in a concentrated manner towards a forced passage area of the fruits; wherein one of the two MAF cameras is located on a left side and the other of the two MAF cameras is located on a right side of the passage area, with vision overlap towards a common passage area, and aligned in opposite positions of a transverse passage line to allow observing broad surface portions of the fruits conveyed through the unit.

7. The system according to claim 1, wherein both cameras generate images synchronized with one and the same signal of pulses proportional to the speed of the fruit conveyor, susceptible of being interpreted with application software incorporated in a suitable control device.

* * * * *